United States Patent [19]
Goodchild et al.

[11] Patent Number: 5,545,729
[45] Date of Patent: Aug. 13, 1996

[54] STABILIZED RIBOZYME ANALOGS

[75] Inventors: John Goodchild, Westborough; Steven M. Nesbitt, Worcester, both of Mass.

[73] Assignee: Hybridon, Inc., Worcester, Mass.

[21] Appl. No.: 361,687

[22] Filed: Dec. 22, 1994

[51] Int. Cl.$^6$ ............................ C07H 21/04; C12Q 1/68; C12Q 1/70; A61K 48/00
[52] U.S. Cl. .................... 536/24.5; 435/6; 435/5
[58] Field of Search .................. 435/6, 5; 514/44; 536/24.5

[56] References Cited

FOREIGN PATENT DOCUMENTS

| W092/07065 | 4/1992 | WIPO . |
| W093/15194 | 8/1993 | WIPO . |
| W093/15187 | 8/1993 | WIPO . |
| W094/10301 | 5/1994 | WIPO . |
| W094/12633 | 6/1994 | WIPO . |

OTHER PUBLICATIONS

Haseloff et al. (1988) *Nature* 334:585–591.
Buzayan et al. (1990) *Nucleic Acids Res.* 18:4447–4451.
Dahm et al. (1990) *Biochim.* 72:819–23.
Goodchild (1990) *Bioconjugate Chem.* 1:165–187.
Odai et al. (1990) *FEBS Lett.* 267:150–152.
Perreault et al. (1990) *Nature* 344:565–567.
Ruffner et al. (1990) *Nucleic Acids Res.* 18:6025–6029.
Goodchild et al. (1991) *Arch. Biochem. Biophys.* 284:386–391.
Koisumi et al. (1991) *Biochem.* 30:5145–5150.
Olsen et al. (1991) *Biochem.* 30:9735–9741.
Perreault et al. (1991) *Biochem.* 30:4020–4025.
Pieken et al. (1991) *Science* 253:314–317.
Agrawal et al. (1992) *Trends Biotechnol.* 10:152–158.
McCall et al. (1992) *Proc. Natl. Acad. Sci. (USA)* 89:5710–5714.
Paolella et al. (1992) *Embo J.* 11:1913–1919.
Benseler et al. (1993) *J. Am. Chem. Soc.* 115:8483–8484.
Ma et al. (1993) *Biochem.* 32:1751–1758.
Ma et al. (1993) *Nucleic Acids Res.* 21:2585–2589.
Thomson et al. (1993) *Nucleic Acids Res.* 21:5600–5603.
Tuschl et al. (1993) *Proc. Natl. Acad. Sci. (USA)* 90:6991–6994.
Ibirbarren et al, "2∝–O–Alkyl Oligoribonucleotides as Antisense Probes", PNAS 87:7747–7751. Oct. 1990.
Sproat et al, "Highly Efficient Chemical Synthesis of 2∝–O–Methyl–Oligoribonucleotides and Tetrabiotonylated Derivatives; Novel Probes Let are Resistant to Degradation by RNA or DNA Specific Nucleoses".

*Primary Examiner*—Stephanie W. Zitomer
*Assistant Examiner*—Dianne Rees
*Attorney, Agent, or Firm*—Lappin & Kusmer LLP

[57] ABSTRACT

Disclosed are stabilized ribozyme analogs having the ability to endonucleolytically cleave a sequence of 3' to 5' linked ribonucleotides. These ribozyme analogs include modifications at specific loop, catalytic core, and flanking region nucleotides which makes them more resistant to nucleases. Also disclosed are methods of preparing and utilizing the ribozyme analogs of the invention, and pharmaceutical formulations and kits containing such ribozyme analogs.

28 Claims, 8 Drawing Sheets

STABILIZED RIBOZYME ANALOGS

BACKGROUND OF THE INVENTION

This invention relates to molecules with endonucleolytic activity and enhanced half-lives useful in the site-specific cleavage of RNA. This invention also relates to the control of gene expression through the degradation of mRNA.

Ribozymes are RNA molecules with catalytic activities including the ability to cleave at specific phosphodiester linkages in RNA molecules to which they have hybridized, such as mRNAs, RNA-containing substrates, and ribozymes themselves.

Ribozymes may assume one of several physical structures, one of which is called a "hammerhead" (Haseloff and Gerlach (1988) *Nature* 334:585–591). A hammerhead ribozyme is composed of a catalytic core containing nine conserved bases, a double-stranded stem and loop structure (helix II), and two regions flanking the catalytic core that are complementary to the target RNA. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to specific ribonucleotide triplet by a transesterification reaction from a 3',5'-phosphate diester to a 2',3'-cyclic phosphate diester. It is currently believed that this catalytic activity requires the presence of specific, highly conserved sequences in the catalytic region of the ribozyme.

Although the endonucleolytic activity of ribozymes has been demonstrated in vitro, their use in vivo has been limited by their susceptibility to RNAses. Furthermore, therapeutics such as ribozymes having greater than 30 or more nucleotides are expensive and difficult to produce in great quantities. Thus, there is a need for smaller molecules with increased nuclease resistance that can be used to cleave RNA in vitro and in vivo, and to control gene expression for in vitro studies and in vivo therapeutic use.

In an effort to protect antisense oligonucleotides from degradative influences in vivo, various structural modifications have been made to these molecules, including the replacement of phosphodiester linkages with non-phosphodiester linkages, the substitution of various sugar groups and bases, the addition of end-capping groups, and the substitution or replacement of existing structures with the self-hybridizing termini (reviewed in Goodchild (1990) *Bioconjugate Chem.* 1:165–187; Agrawal et al. (1992) *Trend Biotechnol.* 10:152–158; WO 93/15194; WO 94/10301; WO 94/12633).

However, modifications which protect an RNA molecule from endonuclease digestion may also affect the catalytic activity of the ribozyme. For example, Perreault et al. (*Nature* (1990) 344:565–567) report that the replacement of ribonucleotides at various conserved positions within the ribozyme sequence with 2'-deoxynucleotides resulted in a 96% decrease of catalytic efficiency. Perreault et al. (*Biochem.* (1991) 30:4020–4025) and Dahm et al. (*Biochim.* (1990) 72:819–23) disclose that the replacement of various 2'-hydroxyl groups with hydrogen atoms reduced the catalytic activity of hammerhead ribozymes. Olsen et al. (*Biochem.* (1991) 30:9735–9741) report that replacing 2'-hydroxyl groups on all adenosine residues by either fluorine or hydrogen decreases the catalytic activity of a ribozyme. Odai et al. (*FEBS Lett.* (1990) 267:150–152) report that replacing the exocyclic amino group of a conserved guanosine residue in the core region with hydrogen reduced catalytic activity. Ruffner et al. (*Nucleic Acids Res.* (1990) 18:6025–6029) and Buzayan et al. (*Nucleic. Acids Res.* (1990) 18:4447–4451) disclose that replacing oxygen atoms by sulfur on various internucleotide phosphate residues reduces catalytic activity. Pieken et al. (*Science* (1991) 253:314–317) disclose that catalytic activity is reduced when various 2'-hydroxyl groups on adenosine residues are replaced with fluorine and when the 2'-hydroxyl groups on cytidine residues are replaced with amine groups. Paolella et al. (*EMBO J.* (1992) 11:1913–1919) have investigated which 2'-hydroxyl groups may or may not be alkylated without loss of catalytic activity.

Other groups have substituted nucleotides within the ribozyme with nucleotide analogs. For example, Usman et al. (WO 93/15187) designed chimeric polymers or "nucleozymes" with ribozyme-like catalytic activity having ribonucleotides or nucleic acid analogs (with modified sugar, phosphate, or base) at catalytically critical sites and nucleic acid analogs or deoxyribonucleotides at non-catalytically critical sites.

Recently, modifications such as a reduction in the length of the helix II structure of the hammerhead ribozyme have been made in an effort to design a more stable molecule without reducing its catalytic activity (see, e.g., Goodchild et al. (1991) *Arch. Biochem. Biophys.* 284:386–391; Tuschl et al. (1993) *Proc. Natl. Acad. Sci.* (USA) 90:6991–6994; McCall et al. (1992) *Proc. Natl. Acad. Sci.* (USA) 89:5710–5714).

Modifications in ribozyme structure have also included the substitution or replacement of various non-core portions of the molecule with non-nucleotidic molecules (see, e.g., Benseler et al. (1993) *J. Am. Chem. Soc.* 115:8483–8484; Ma et al. (1993) *Biochem.* 32:1751–1758; Ma et al. (1993) *Nucleic Acids Res.* 21:2585–2589; and Thomson et al. (1993) *Nucleic Acids Res.* 21:5600–5603).

Thus, ribozymes with improved resistance to endonucleolytic digestion are desirable, and there continues to be a need for such catalytic molecules.

SUMMARY OF THE INVENTION

The present invention provides catalytic oligonucleotides or stabilized ribozyme analogs capable of endonucleolytically cleaving single-stranded RNA, and having increased nuclease resistance due to the presence of nucleotide analogs at specified positions.

It has been discovered that in human serum and in extracts of CEM cells, degradation of ribozymes first involves endonuclease attack at non-base-paired pyrimidines in the flanking sequences, the catalytic core, or in the loop of helix II. Of these, only bases C3 and U4 are necessary and cannot be replaced by other bases. These findings have been exploited to develop the present invention which, in one aspect, includes a "stabilized ribozyme analog" or ribozyme-like RNA-containing molecules having an endonucleolytic activity and structure similar to a hammerhead ribozyme, but in contrast, having nucleotide analogs substituted into various positions in the ribozyme, thereby bestowing it with greater nuclease resistance.

The stabilized ribozyme analog of the invention includes a helix II having a 3' terminus and comprising a stem region and a loop region. As used herein, the term "helix II" refers to the double-stranded, coiled helical structure in hammerhead ribozymes having at one end a single-stranded loop, as described by Haseloff et al. (*Nature* (1988) 334:585–591).

The stem region also has a 3' terminus and 5' terminus and includes a plurality of 3' to 5' covalently-linked, self-hybridized nucleotides.

As used herein, the term "self-hybridizing" refers to nucleotides in the stem region of the helix II which are complementary to each other, and which form normal Watson-Crick base pairs. This stem region has two complementary nucleotidic strands which include at least one nucleotide on one stand and one nucleotide on the other strand which base pair together. In one non-limiting embodiment, the stem of the helix II has from 2 to 8 base-pairs.

In other preferred embodiments, any or all pyrimidines in the stem of helix II are 2'-O-alkylated. Thus, in some embodiments, the stem region contains at least one 2'-O-alkylated nucleotide(s) or is all 2'-O-alkylated. The term "2-O-alkylated" refers to nucleosides or nucleotides having the 2' hydroxyl group on its ribose sugar substituted with an alkyl group such as a methyl, ethyl, propyl, or butyl group. In one particular embodiment, nucleotides at hammerhead ribozyme positions 10.3, 10.4, 11.1, and 11.2 are 2'-O-alkylated (see, Haseloff et al., ibid.) for nomenclature).

The loop region of the helix II is covalently linked to the stem region at its 3' and 5' termini and comprises a plurality of 3' to 5' covalently-linked nucleotides including at least two modified nucleotides which are 2'-O-alkylated, purines, or a combination thereof, at positions L2.2 and L2.3 (see, Haseloff et al., (ibm.) for nomenclature).

As used herein, the term "modified nucleotide" refers to a nucleotide which has been 2'-O-alkylated, i.e., the 2' hydroxyl group on its ribose sugar substituted with an alkyl group, or refers to a purine which has been substituted for a pyrimidine.

In some embodiments, all of the nucleotides of the loop region are modified. In other embodiments, the nucleotides at positions L2.2 and L2.3 are methylphosphonate, phosphoramidate, or phosphoramidate analogs. In yet other embodiments the nucleotides in the loop region are covalently linked with phosphodiester, alkylphosphonate, phosphorothioate, phosphorodithioate, alkylphosphonothioate, phosphoramidate, phosphate ester, carbamate, carbonate, acetamidate, or carboxymethyl ester internucleotide linkages, or with a combination of such linkages.

The ribozyme analog further includes first and second catalytic core regions, each comprising a plurality of 3' to 5' covalently-linked nucleotides, and each having a 3' terminus and a 5' terminus. The 3' terminus of the first catalytic core region is covalently linked to the 5' terminus of the stem region, and the 5' terminus of the second catalytic core region is covalently linked to the 3' terminus of the stem region. The first catalytic core region further includes at least one 2'-O-alkylated or purine nucleotide at position 7 (see, Haseloff et al. (ibid.) for nomenclature). In addition, the nucleotides at positions 3 and 4 of the first catalytic core region are 2'-O-alkylated. In another embodiment, the linkage between nucleosides 6 and 7 is a methylphosphonate or phosphoramidate.

To the 5' terminus of the first nucleotidic core region is covalently linked a first flanking region at its 3' terminus, and to the 3' terminus of a second nucleotidic core region is covalently linked the 5' terminus of the second flanking region. These first and second flanking regions each include a plurality of 3' to 5' covalently-linked nucleotides, and each has a 3' terminus and 5' terminus. At least a portion of the first flanking region is complementary to a first target region of a substrate RNA molecule, and at least a portion of the second flanking region is complementary to a second target region of the substrate RNA molecule.

In preferred embodiments, the first and/or the second flanking region contains at least one 2'-O-alkylated nucleotide. In other embodiments at least four of the nucleotides in the first and second flanking regions are 2'-O-alkylated. In another embodiment, all of the pyrimidines in the first and second flanking regions are 2'-O-alkylated. In yet another embodiment, all of the nucleotides in the first and/or second flanking region are 2'-O-alkylated, with the exception of the one at position 15.1 (see, Haseloff et al. (ibid.) for nomenclature). In other embodiments, the nucleosides in the first and second flanking regions are covalently linked with phosphodiester, alkylphosphonate, phosphorothioate, phosphate ester, phosphorodithioate, alkylphosphonothioate, phosphoramidate, carbamate, carbonate, acetamidate, or carboxymethyl ester internucleotide linkages, or a combination of such linkages. In preferred embodiments, the flanking regions each include at least four nucleotides. In one embodiment, the four nucleotides of the first flanking region are complementary to a first set of nucleotides of a target RNA, and the four nucleotides of the second flanking region are complementary to a second set of nucleotides of the target RNA, the first and second sets being exclusive of each other. In another embodiment, both the first and second flanking regions include at least six nucleotides.

As used herein, the terms "target RNA" and "substrate RNA" refers to an oligoribonucleotide composed of 3' to 5' covalently-linked ribonucleotides to which the flanking regions of the ribozyme analog hybridize, and which the ribozyme analog recognizes and cleaves.

In some embodiments, at least two of the nucleosides of the ribozyme analog are covalently linked by a phosphodiester, alkylphosphonate, and/or phosphoramidate internucleoside linkage. In one specific embodiment, at least two nucleosides in the ribozyme analog are linked via a methylphosphonate linkage.

Another aspect of the invention is a method of controlling the expression of a substrate RNA molecule. In this method, a stabilized ribozyme analog of the invention is provided and used to contact the RNA. By "provided" is meant to supply commercially or otherwise, make available, or prepare. The first flanking region of the ribozyme analog hybridizes to the first target region of the substrate RNA, the second flanking region hybridizes to the second target region of the substrate RNA, thereby enabling the stabilized ribozyme analog to cleave the substrate RNA. In this way, the expression of the substrate RNA, e.g., its ability to be translated into protein, is controlled.

In some embodiments of the method, the substrate RNA to be cleaved is also contacted a facilitator oligonucleotide at the same time as it is contacted with the ribozyme analog. As used herein, a "facilitator oligonucleotide" encompasses oligodeoxyribonucleotides, oligoribonucleotides, or chimeras which are complementary and hybridizable to a sequence of ribonucleotides on the RNA substrate which is adjacent the first or second target regions targeted by either flanking regions of the ribozyme analog (see, WO 93/15194).

In another aspect of the invention, a method of site-specifically cleaving a single-stranded, RNA-containing substrate is provided. As used herein, the term "site-specifically cleaving" refers to enzymatically cutting the phosphate backbone of the substrate RNA molecule before or after a particular sequence of ribonucleotides. The method includes providing a stabilized ribozyme analog of the invention and then contacting the RNA-containing substrate molecule with the ribozyme analog such that the first flanking region of the ribozyme analog hybridizes to the first target region of the substrate RNA, and the second flanking region of the ribozyme analog hybridizes to the second target region of the substrate RNA molecule thereby enabling the ribozyme analog to site-specifically cleave the RNA substrate. In some embodiments, the method further includes contacting the substrate RNA molecule with a facilitator oligonucleotide at the time it is contacted with the ribozyme analog.

The invention also provides a kit including at least one stabilized ribozyme analog of the invention. In some embodiments, the kit further includes a facilitator oligonucleotide and/or an RNA ligase. Other kits also contain a physiologically acceptable carrier.

Still another aspect of the invention is a therapeutic formulation including at least one stabilized ribozyme analog of the invention in a physiologically acceptable carrier. In some embodiments, the formulation further includes a facilitator oligonucleotide.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patent, allowed patent applications, and articles cited herein are hereby incorporated by reference.

Figure 1:
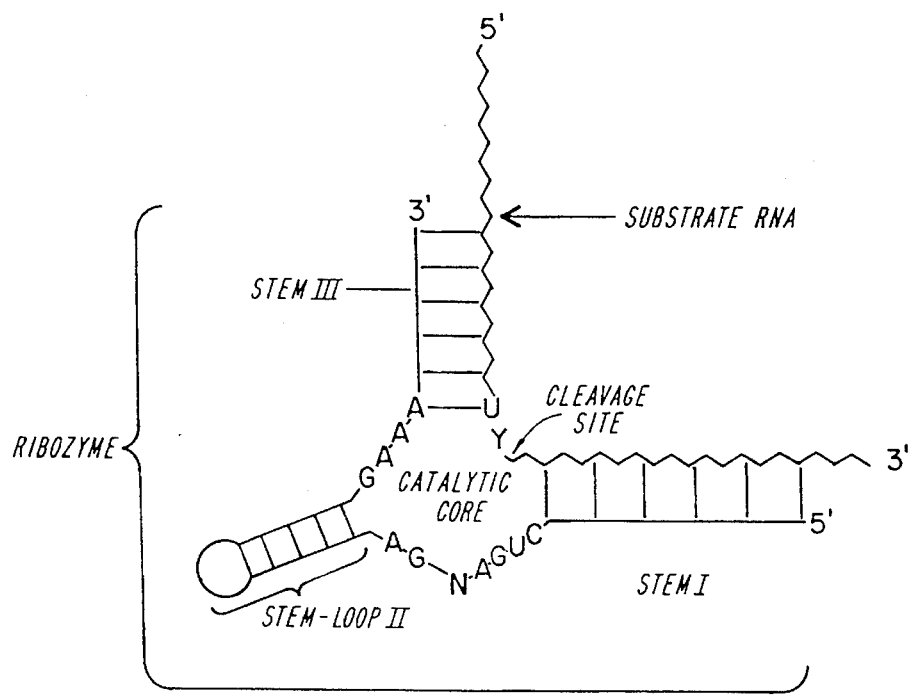
FIG. 1 is a diagrammatic representation of a consensus hammerhead ribozyme hybridized with a substrate RNA, wherein the conserved ribonucleotides (C,U,G,A,G,A,G,A, A) and the non-conserved nucleotide (N) are in the catalytic core of the ribozyme, and wherein cleavage occurs on the 3' side of nucleotide (Y) in the substrate RNA.

The hammerhead ribozyme, as engineered by Haseloff and Gerlach (*Nature* (1988) 334:585–591), is depicted in FIG. 1. It is composed of a helical structure (helix II) made up of a single-stranded loop region and a double-stranded stem region connecting two portions of a catalytic core having nine conserved ribonucleotides, and flanked by two regions complementary to the target RNA. These flanking regions enable the ribozyme to bind to the target RNA specifically by forming double stranded stems I and III. Current belief is that the nucleotide sequence of the ribozymal catalytic core region must be largely conserved in order to maintain the ability of the ribozyme to cleave single-stranded RNA (Koizumi et al. (1991) *Biochem.* 30:5145–5150; Thomson et al. (1993) *Nucleic Acids Res.* 21:5600–5603). However, it has now been discovered that this cleavage can be accomplished with molecules containing ribozyme analogs substituted for particular nucleotides within the stem and/or loop of helix II, the catalytic core, and the flanking regions, and that these ribozyme analogs have improved nuclease resistance (i.e., are stabilized).

These findings have been exploited to develop the present invention, which provides stabilized analogs of hammerhead ribozymes containing such nucleotide analogs which have the ability to endonucleolytically cleave single-stranded RNA and RNA-containing substrates. Thus, stabilized ribozyme analogs according to the invention are useful as RNA-specific restriction endonucleases, and as such, in combination with RNA ligases, allow for the preparation of recombinant RNA molecules.

Figure 2:
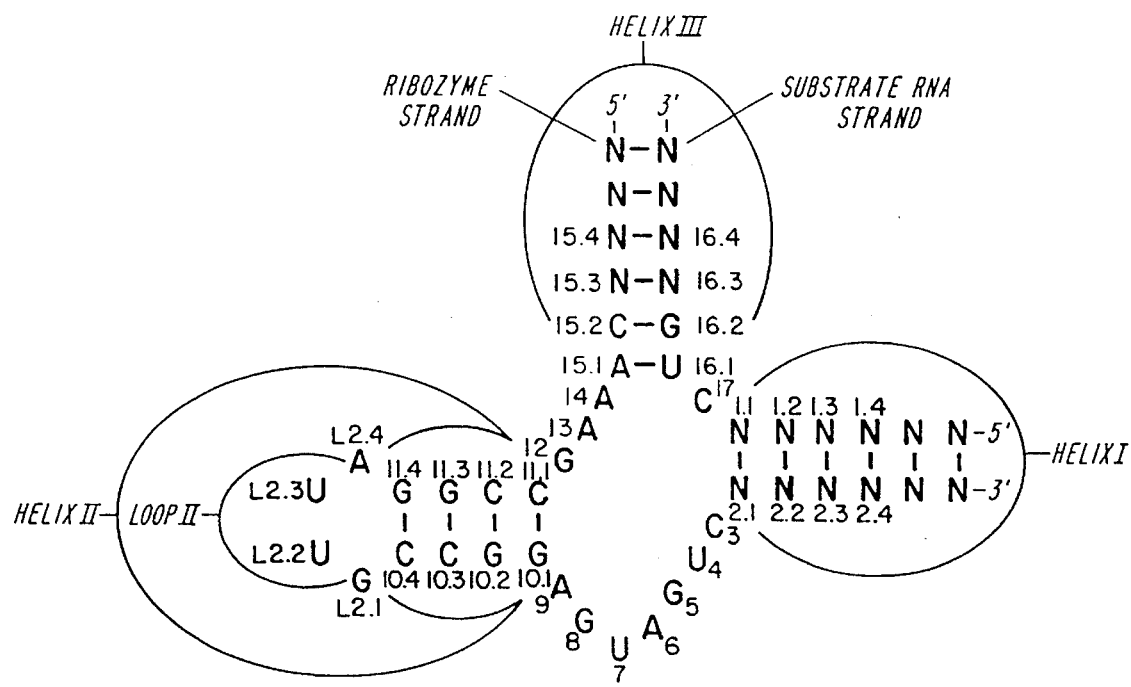
FIG. 2 is a schematic representation of a hammerhead ribozyme hybridized to its substrate, and the standard position numbers of the nucleotides of this complex.

The helix II stem region of the stabilized ribozyme analogs of the invention are composed of at least four, but preferably 6 to 12 nucleotides which are self-hybridizing. This region is numbered 10.1 to 10.4 and 11.1 to 11.4 in FIG. 2, which delineates the standard positions numbers of the nucleotides in the hammerhead ribozyme as described in the art (see, e.g., Pley et al. (1994) *Nature* 372:68; Hertel et al. (1992) *Nucleic Acids Res.* 20:3252). The loop region of helix II has at least 2, and preferably 4 or more unhybridized nucleotides which, in FIG. 2, are at positions L2.1 to L2.4.

The catalytic core of the ribozyme analogs of the invention is composed of first and second catalytic core regions consisting of nucleotides at positions 3–9, and 12–14 in FIG.

2. This region has conserved nucleotides or nucleotides which are believed to be present for catalytic activity.

The catalytic core regions are flanked by first and second flanking regions, each of which contains nucleotide sequences which are complementary to, and hybridizable with, target regions on the RNA substrate to be cleaved. The target regions complementary to the flanking regions are separated by one nucleotide. The nucleotides making up the flanking regions are of deoxyribonucleotides, analogs of deoxyribonucleotides, ribonucleotides, analogs of ribonucleotides, or a combination thereof, with the 5' end of one nucleotide or nucleotide analog and the 3' end of another nucleotide or nucleotide analog being covalently linked. These flanking regions are at least four nucleotides in length, but are preferably six to fifty nucleotides long, with flanking regions of six to fifteen nucleotides being the most common. In FIG. 2, these nucleotides are at positions 1.1 to 1.6 and 2.1 to 2.6.

Figure 3A:
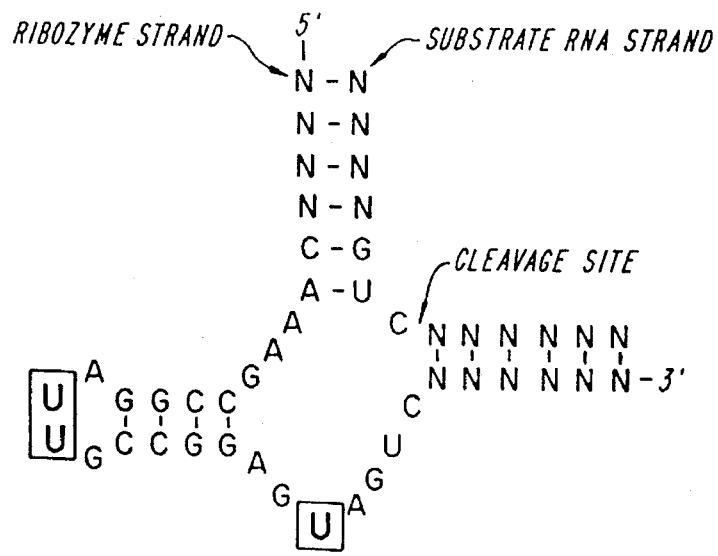
FIG. 3A is a diagrammatic representation of R48, a stabilized ribozyme analog of the invention hybridized with a substrate RNA, wherein the 2'-O-alkylated nucleotides are boxed.
Figure 3B:
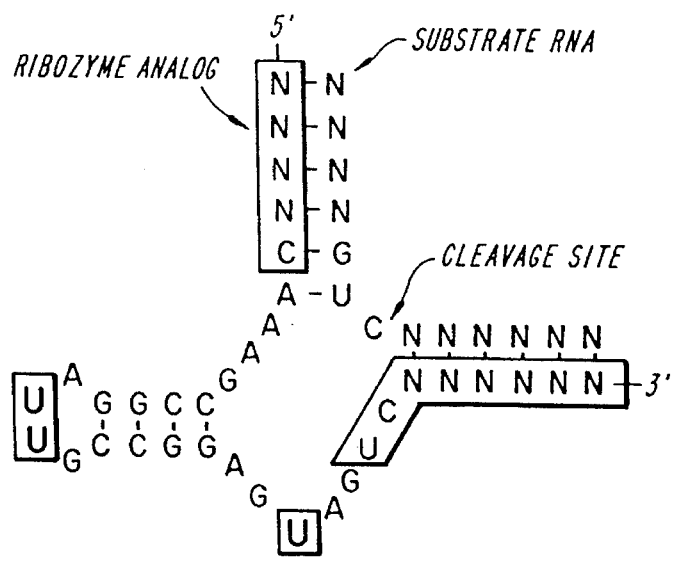
FIG. 3B is a diagrammatic representation of R52, a stabilized ribozyme analog of the invention hybridized with a substrate RNA, wherein the 2'-O-alkylated nucleotides are boxed.
Figure 3C:
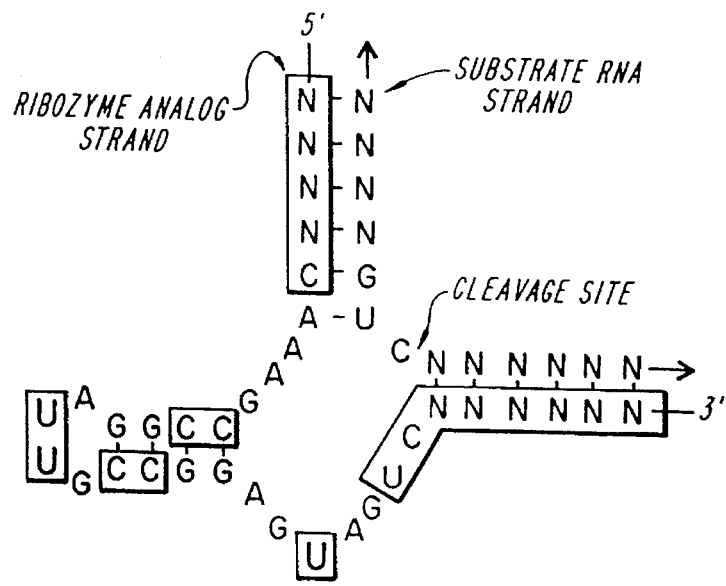
FIG. 3C is a diagrammatic representation of R56, a stabilized ribozyme analog of the invention hybridized with a substrate RNA, wherein the 2'-O-alkylated nucleotides are boxed.
Figure 3D:
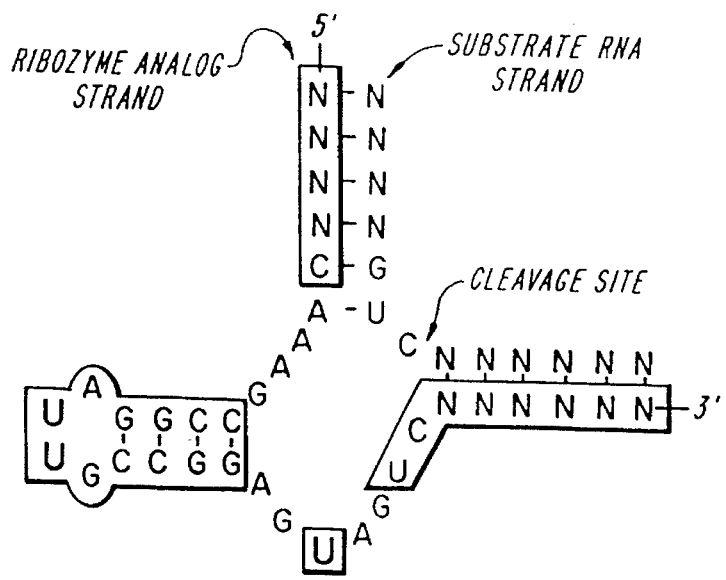
FIG. 3D is a diagrammatic representation of R53, a stabilized ribozyme analog of the invention hybridized with a substrate RNA, wherein the 2'-O-alkylated nucleotides are boxed.
Figure 3E:
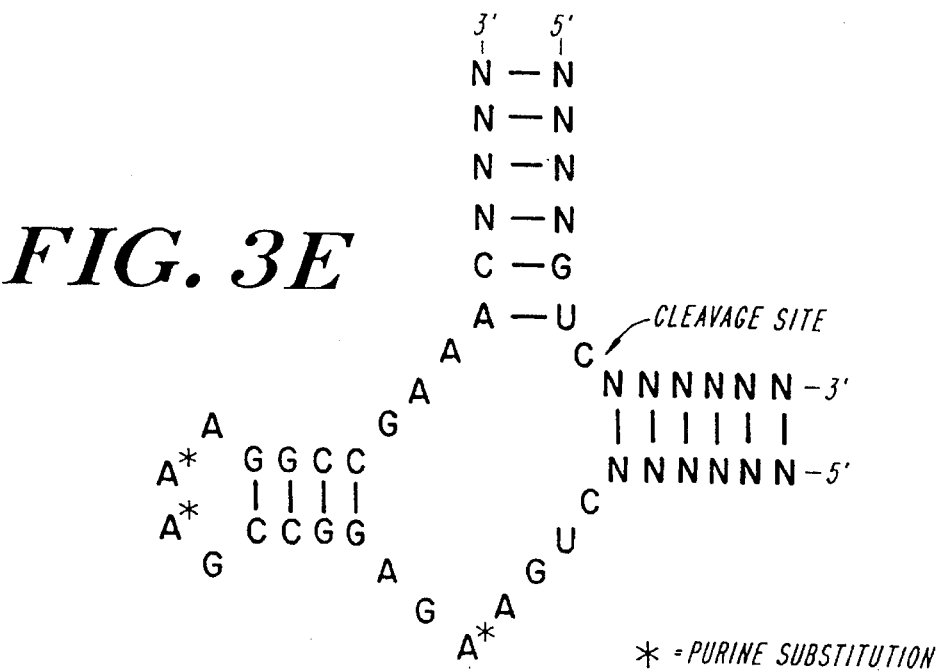
FIG. 3E is a diagrammatic representation of R44, a stabilized ribozyme analog of the invention hybridized with a substrate RNA, wherein the nucleotides marked with an asterisk have been purine-substituted.

The ribozyme analogs of the invention are structurally distinct from an unmodified hammerhead ribozyme in that any pyrimidine in the loop of helix II, as well as those at positions 3, 4 and 7 (see, e.g., FIGS. 3A–3D), are made resistant to ribonucleases by 2'-O-alkylation. Those in the loop of helix II and at position 7 may alternatively be substituted by purine nucleotides (see, e.g., FIG. 3E). In addition, at least all the pyrimidine nucleotides in the flanking sequences are made resistant to ribonucleases by 2'-O-alkylation or by modification of internucleoside phosphates to thiophosphates or methylphosphonates, etc. Preferably, purine nucleotides in the flanking sequences are also modified in the same way. Further, either the pyrimidine nucleotides in the stem of helix II or both the pyrimidine and purine nucleotides may be made resistant to ribonucleases by 2'-O-alkylation.

The ribozyme analogs may be further substituted at nucleotides at positions 3 and 4 of the catalytic core region, positions 2.1–2.6 of the first flanking region, and/or positions 15.2–15.6 of the second flanking region, and/or at all of the positions in the helix II. FIGS. 3A to 3E depict several nonlimiting embodiments containing nucleotide substitutions at "boxed" locations. Such substitution(s) enhance stability in the presence of nucleases, and do not affect activity to any great extent in the presence of a facilitator oligonucleotide.

The structural characteristics of some representative ribozyme analogs of the invention illustrated schematically shown in FIGS. 3A to 3E are summarized below in TABLE 1.

TABLE 1

| Ribozyme Analogs | Number of Substituted Nucleotides | | | | | SEQ ID NO: |
|---|---|---|---|---|---|---|
| | L | S | C | F1 | F2 | |
| R52 | 2 | 0 | 3 | 6 | 5 | 1 |
| R53 | 4 | 8 | 3 | 6 | 5 | 1 |
| R48 | 2 | 0 | 1 | 0 | 0 | 1 |
| R56 | 2 | 4 | 3 | 6 | 5 | 1 |
| R44 | 2 | 0 | 1 | 0 | 0 | 1 |
| R49 | 3 | 0 | 3 | 6 | 5 | 3 |
| R6 | 2 | 8 | 1 | 0 | 0 | 1 |
| R7 | 4 | 8 | 1 | 0 | 0 | 1 |
| R8 | 2 | 0 | 3 | 0 | 0 | 1 |
| R9 | 2 | 0 | 3 | 1 | 0 | 1 |
| R10 | 2 | 0 | 3 | 6 | 5 | 1 |
| R11 | 2 | 0 | 3 | 6 | 5 | 1 |
| R12 | 4 | 8 | 3 | 6 | 5 | 1 |

TABLE 1-continued

| Ribozyme Analogs | Number of Substituted Nucleotides | | | | | SEQ ID NO: |
|---|---|---|---|---|---|---|
| | L | S | C | F1 | F2 | |
| R13 | 2 | 4 | 3 | 6 | 5 | 1 |
| R14 | 2 | 0 | 1 | 5 | 5 | 1 |
| R15 | 2 | 8 | 3 | 4 | 3 | 2 |
| R16 | 4 | 8 | 3 | 10 | 5 | 3 |
| R17 | 4 | 6 | 1 | 5 | 5 | 3 |

L = loop of helix II
S = stem of helix II
C = catalytic core
F1 = flanking region I
F2 = flanking region II These combinations of modified positions are different from those described by Paolella et al. (1992) *EMBO J.* 11:1913–1919) who determined which 2"-hydroxyl groups are necessary for catalytic activity rather than which 2'-hydroxyl groups lead to rapid digestion by ribonucleases in human serum.

Useful substitutions at the various nucleotide positions described above include purine nucleotides, deoxynucleotides, 2'-O-alkylated nucleotides, nucleotide methylphosphonates, and nucleotide phosphoramidates. Preferred substitutions include a 2'-O-alkylated nucleotides such as 2'-O-methyls, 2'-O-propyls, and 2'-O-butyls. The most preferred nucleotide analog is a 2'-O-methyl.

The ribozyme analogs can be prepared by art-recognized methods such as phosphoramidate or H-phosphonate chemistry which can be carried out manually or by an automated synthesizer using standard H-phosphonate chemistry as described in U.S. Pat. No. 5,149,789, or using standard phosphoramidite chemistry (see, e.g., Beaucage (*Meth. Mol. Biol.* (1993) 20:33–61); Damha et al. (in *Protcol for Oligonucleotides and Analogs; Synthesis and Properties* (Agrawal, ed.) (1993) Humana Press, Totowa, N.J., pp. 81–114); or Uhlmann et al. (*Chem. Rev.* (1990) 90:534–583).

The ribozyme analog may also be modified in a number of ways for protection against nuclease digestion, without preventing hybridization of the ribozyme analog to substrate RNAs. For example, the nucleosides of the flanking regions and other nucleotidic portions of the ribozyme analog may be covalently linked by other than phosphodiester internucleoside linkages between the 5' end of one nucleoside and the 3' end of another nucleoside, in which the 3' phosphate has been replaced with any number of chemical groups. Examples of such known chemical groups include alkylphosphonates, phosphoramidates, carbamates, acetamidate, carboxymethyl esters, carbonates, and phosphate esters.

Other modifications include those which are internal or at the end(s) of the nucleotidic core or flanking region(s) and include additions to the internucleoside phosphate linkages, such as cholesteryl, or diamine compounds with varying numbers of carbon residues between the amino groups, and terminal ribose, deoxyribose, and phosphate modifications. Examples of such modified flanking regions include nucleotide sequences having a modified base and/or sugar such as arabinose instead of ribose, or a 3', 5'-substituted nucleoside having a sugar which, at both its 3' and 5' positions is attached to a chemical group other than oxygen or phosphate. Other modified nucleotide sequences are capped with a nuclease resistance-conferring bulky substituent or self-hybridized region at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides is well known in the art (reviewed in Agrawal et al. (1992) *Trends Biotechnol.* 10:152–158; in Goodchild (1990) *Bioconjugate Chem.* 2:165–187); Zon in *Protcols for Oligonucleotides and Analogs* (Agrawal, ed.) Humana Press, Totawa, N.J. (1994) Vol. 20, pp. 165–189). For example, nucleotides can be covalently linked using art-recognized techniques such as phosphoramidite, H-phosphonate, or methylphosphonamidite chemistry.

Using the methods described herein, representative ribozyme analogs R52 (FIG. 3B), R53 (FIG. 3D), and R56 (FIG. 3C) were synthesized and tested for their stability in nuclease-containing human serum. The results shown in FIG. 4 demonstrate that these ribozyme analogs are greatly resistant to nucleases present in the serum in comparison to R22 (SEQ ID NO:1), an unsubstituted ribozyme control which underwent almost instantaneous degradation.

Figure 5:
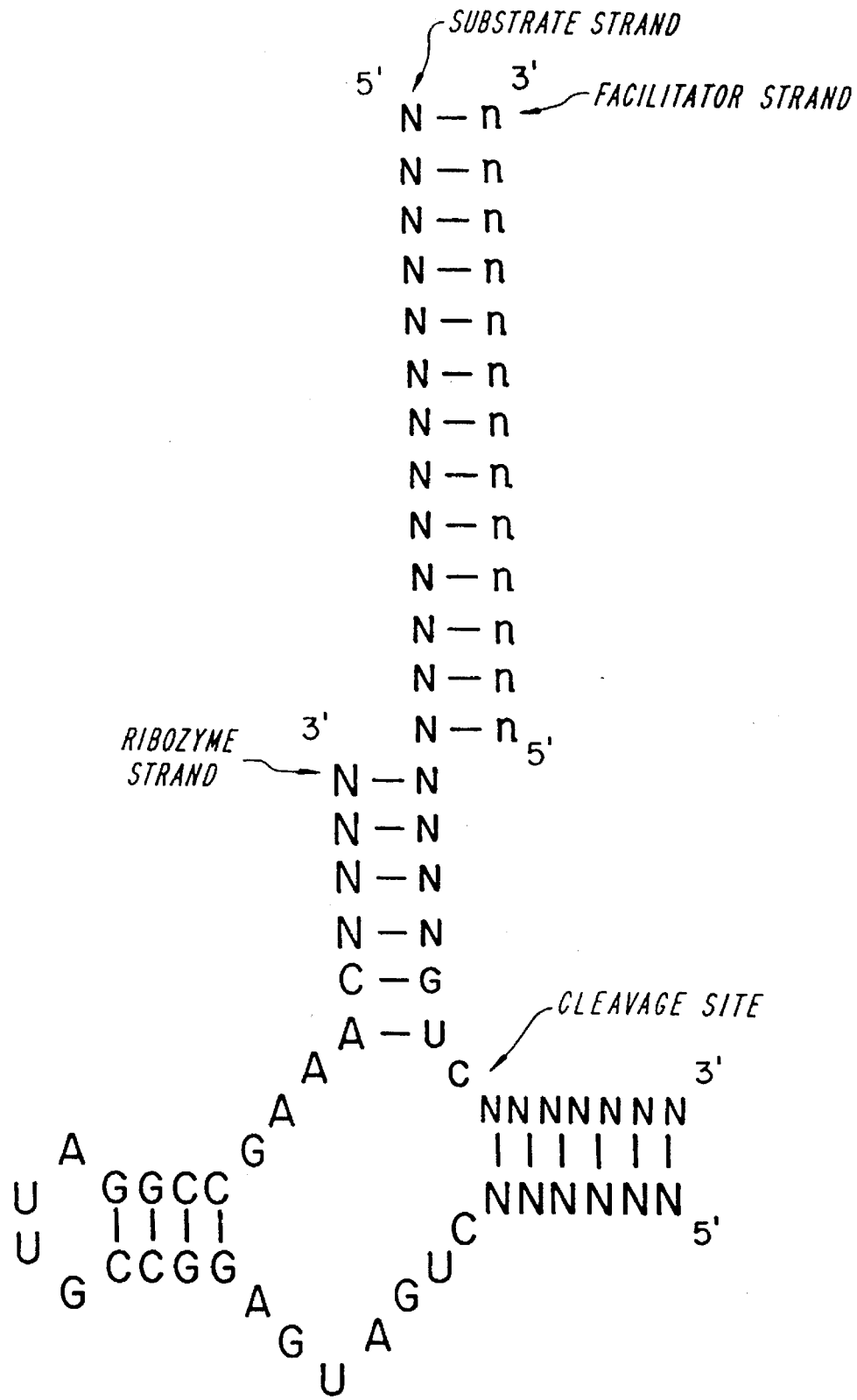
FIG. 5 is a diagrammatic representation of a stabilized ribozyme analog of the invention and facilitator oligonucleotide hybridized with a substrate RNA.

The cleavage abilities of the ribozyme analogs of the invention may be enhanced by introducing a facilitator oligonucleotide into the system which hybridizes adjacent to the ribozyme analog (see, WO 93/15194). Such a facilitator oligonucleotide may be selected to bind to a target sequence on the substrate RNA contiguous with the RNA substrate sequence to which a flanking region binds at the 5' or the 3' side of the ribozyme analog. The catalytic complex formed by the substrate RNA, ribozyme analog, and facilitator oligonucleotide is depicted in FIG. 5.

In some situations, a combination of two facilitator oligonucleotides may be employed, where one facilitator is hybridized to the substrate RNA directly adjacent the nucleotide sequence hybridized to the first (5') flanking sequence of the ribozyme analog, and the other facilitator is hybridized to the substrate RNA directly adjacent the nucleotide sequence hybridized to the second (3') flanking sequence of the ribozyme analog. Alternatively, a plurality of facilitators may be employed to enhance ribozyme analog activity. For example, in a system employing three facilitators, two facilitators can bind contiguously to the RNA substrate sequence complementary to first (5') flanking sequence, while a single additional facilitator can bind contiguously to the RNA substrate sequence complementary to the second (3') flanking region. Those skilled in the art will recognize that a variety of other combinations are also possible.

In addition, facilitator oligonucleotides may have a nucleotide sequence complementary to regions of the RNA substrate that are not immediately contiguous with the substrate sequences complementary to the ribozyme analog flanking sequences. For example, the facilitator may be synthesized such that, when the ribozyme analog and facilitator oligonucleotide are bound to the substrate RNA, a small gap of from one to about five oligonucleotides exists between the ribozyme analog and the facilitator oligonucleotide. Usually, the gap between the facilitator and the ribozyme analog will be between 0 (zero) and 2 nucleotides. Most often, there will be no nucleotide gap between the facilitator and the ribozyme analog.

The facilitator oligonucleotides of the present invention typically have between about 5 and 50 nucleotides. More preferred facilitator oligonucleotides comprise between about 5 and 15 deoxyribonucleotides. Particularly preferred facilitators according to the invention comprise about 13 nucleotides. Selection of a facilitator of a specific length is related to the length of the ribozyme analog flanking sequences. In addition, some facilitator deoxynucleotides may have a sequence of nucleotides, a portion of which is complementary to the RNA substrate sequence, and a portion of which is not complementary to the substrate RNA sequence.

Facilitator oligonucleotides can be synthesized on automated DNA synthesizers or manually from DNA templates. They may be synthesized and subsequently modified to include moieties which will influence the rate of substrate cleavage by the ribozyme analog, increase uptake by cells, or increase resistance to degradation. For example, by increasing the number of bases of the substrate RNA bound near the cleavage site, facilitators permit use of faster acting ribozyme analogs with shorter flanking sequences. In viral applications, facilitators might be of dual benefit in also directing cleavage of the viral RNA by endogenous ribonuclease H.

Figure 6A:
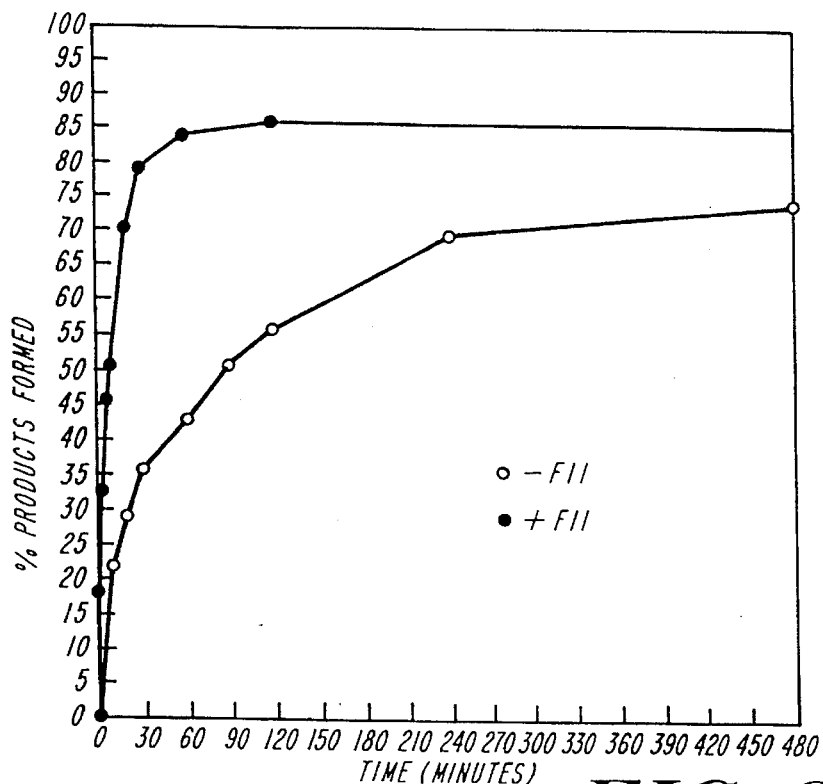
FIG. 6A is a graphic representation of the cleavage activity of R22, a ribozyme control in the presence (-●-) and absence (-o-) of a facilitator oligonucleotide.
Figure 6B:
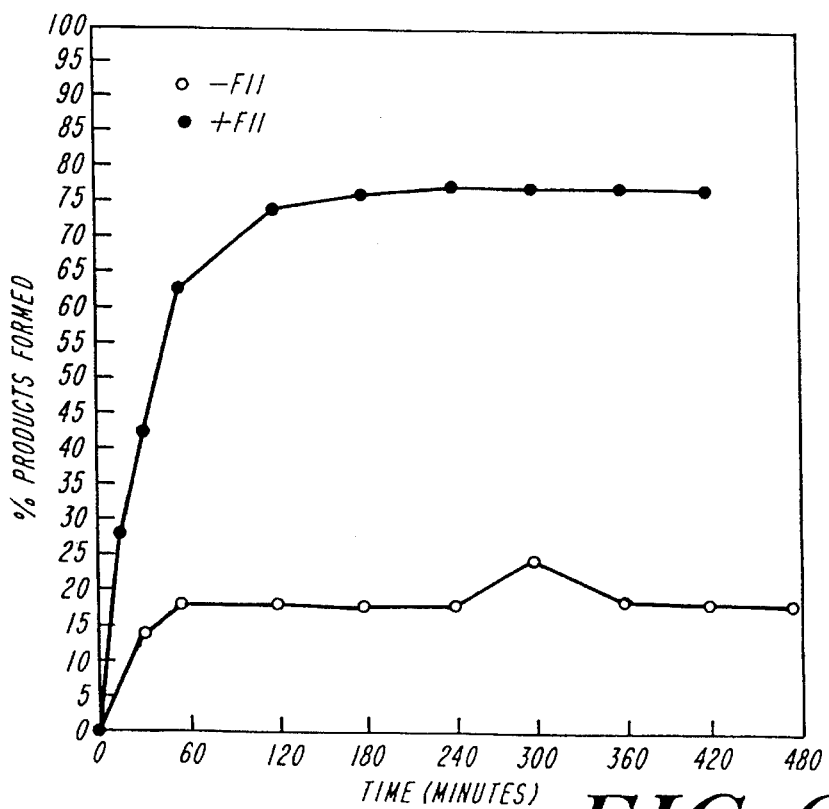
FIG. 6B is a graphic representation of the cleavage activity of R52, a stabilized ribozyme anallog of the invention in the presence (-●-) and absence (-o-) of a facilitator oligonucleotide.
Figure 6C:
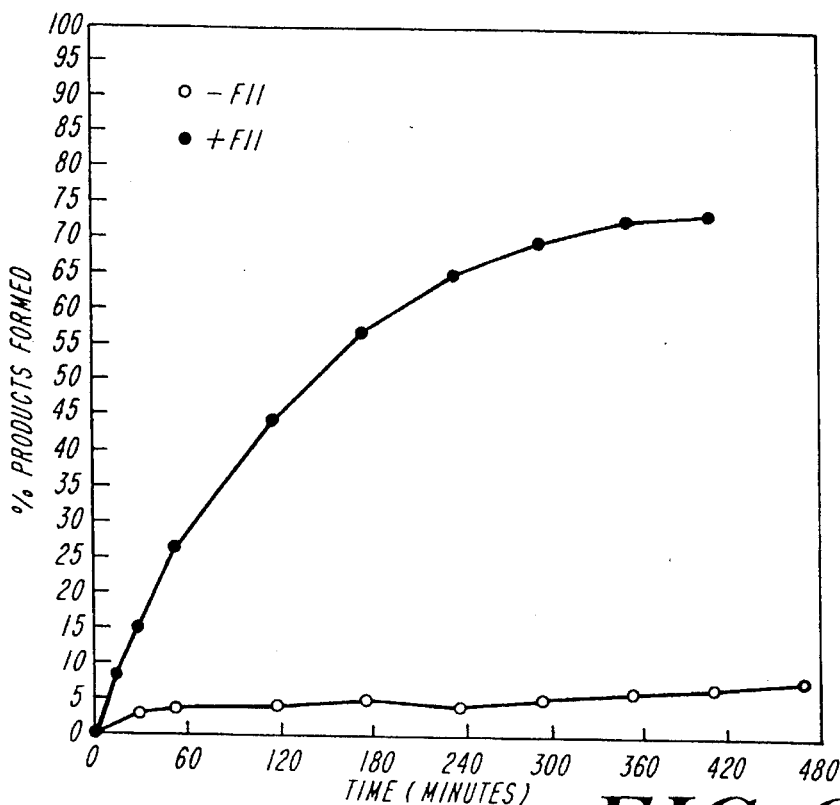
FIG. 6C is a graphic representation of the cleavage activity of R53, another stabilized ribozyme analog of the invention in the presence (-●-) and absence (-o-) of a facilitator oligonucleotide.
Figure 6D:
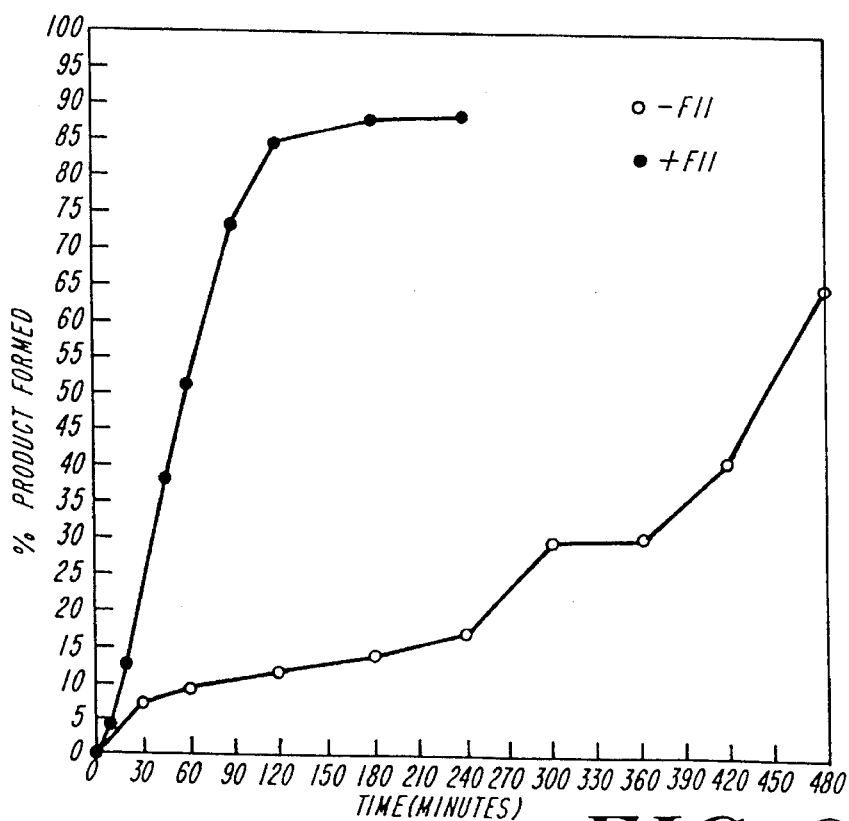
FIG. 6D is a graphic representation of the cleavage activity of R56, yet another stabilized ribozyme analog of the invention in the presence (-●-) and absence (-o-) of a facilitator oligonucleotide.
Figure 6E:
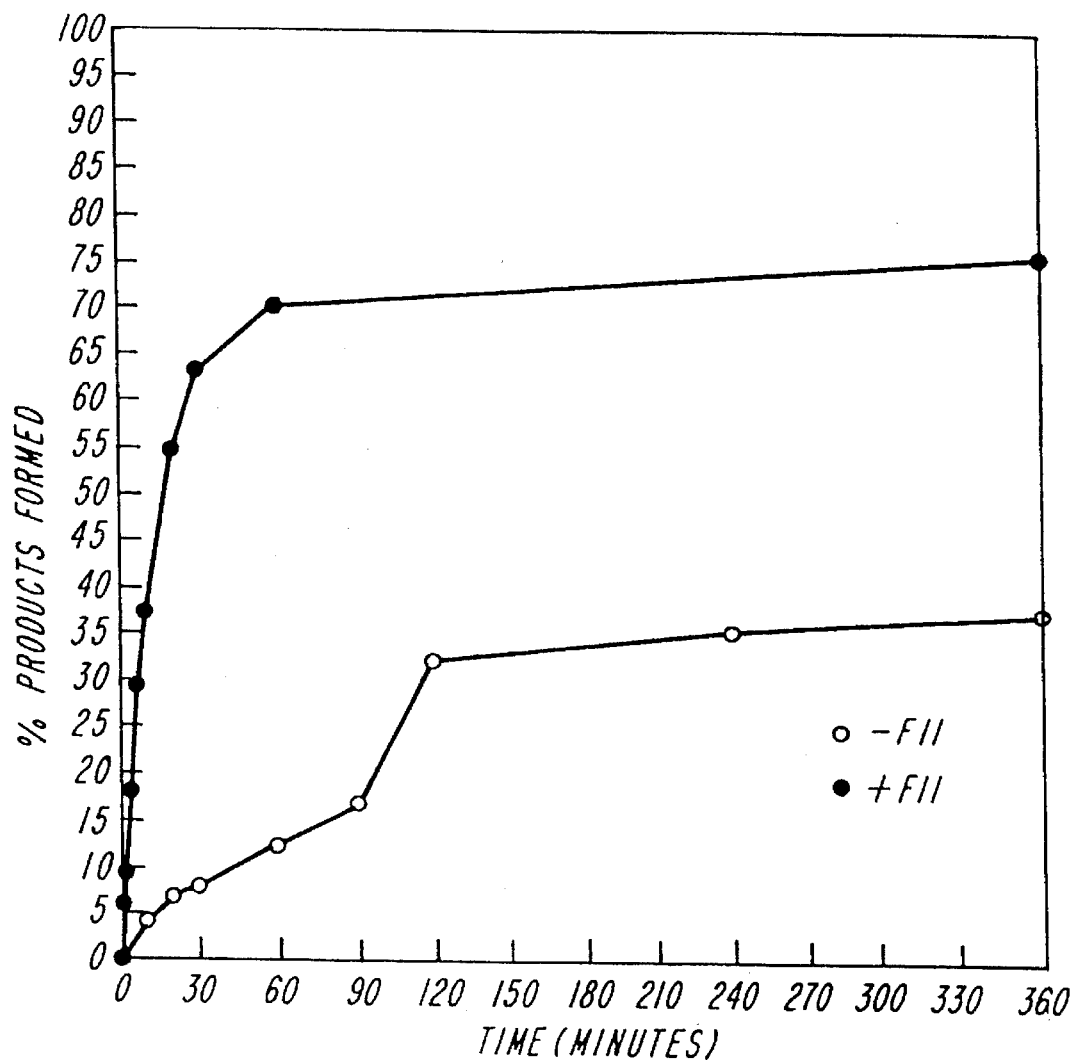
FIG. 6E is a graphic representation of the cleavage activity of R44, yet another stabilized ribozyme analog of the invention in the presence (-●-) and absence (-o-) of a facilitator oligonucleotide.
Figure 1:
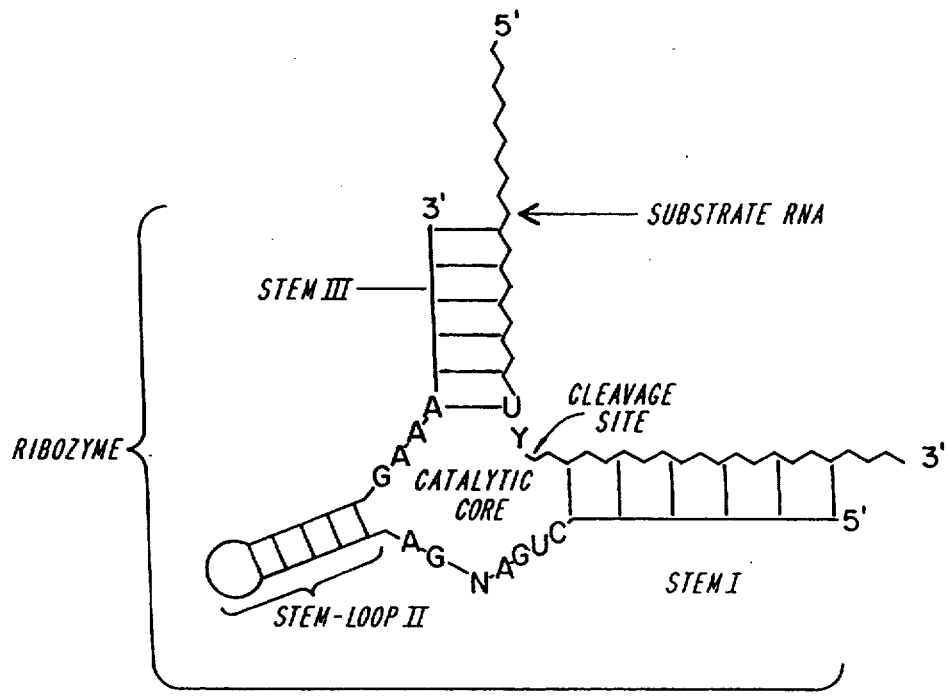
Figure 2:
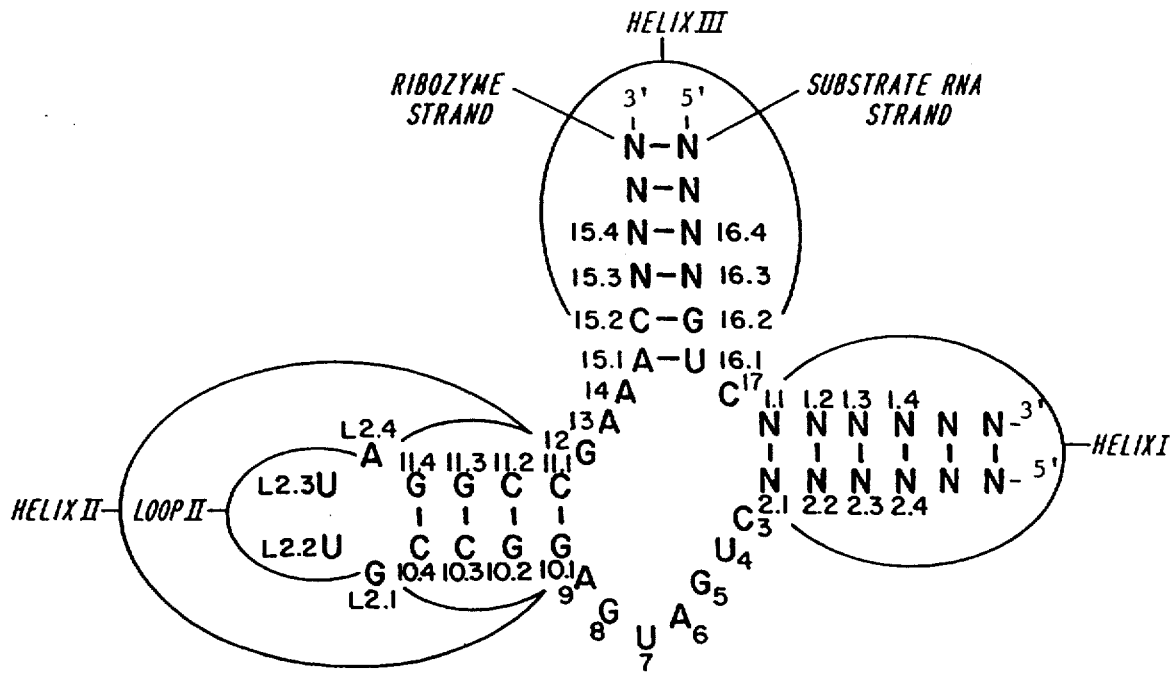
Figure 3A:
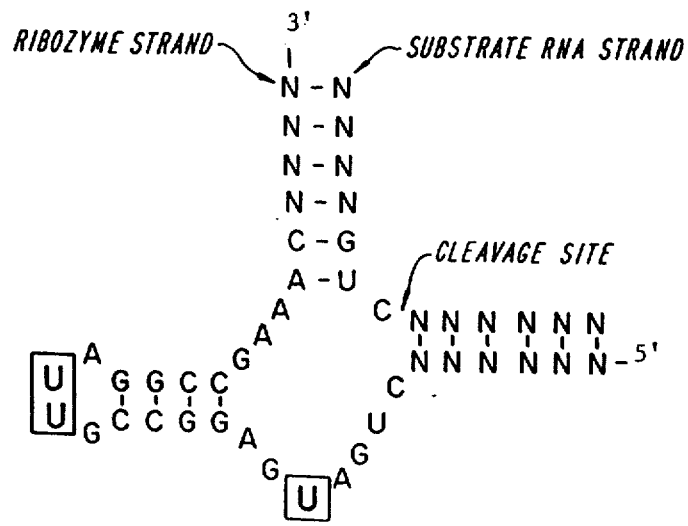
Figure 3B:
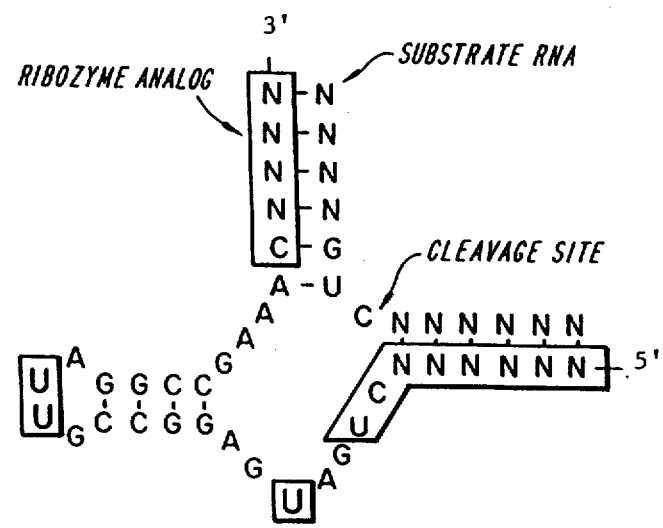
Figure 3C:
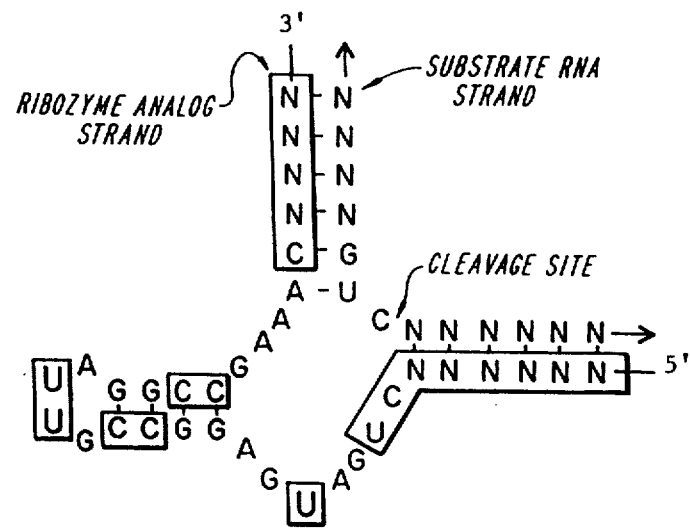
Figure 3D:
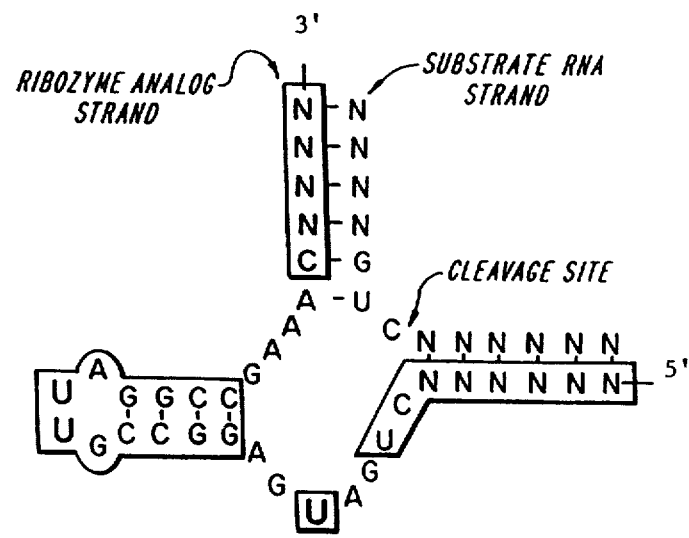

To demonstrate the catalytic capabilities of the stabilized ribozyme analogs of the invention and ability of a facilitator oligonucleotide to enhance these capabilities, the following study was performed. Ribozyme control R22 and stabilized ribozyme analogs R52, R53, R56, R44 and R50 were incubated with substrate RNA in the absence and presence of a facilitator oligonucleotide (F1). The results shown in FIGS. 6B to 6E demonstrate that the stabilized ribozyme analogs of the invention, in combination with a facilitator oligonucleotide, have comparable catalytic activity to the ribozyme control (FIG. 6A).

The stabilized ribozyme analogs of the invention can be provided for any method of use in the form of a kit including a container of a stabilized ribozyme analog of the invention, of mixtures of different stabilized ribozyme analogs, of stabilized ribozyme analog(s) and facilitator oligonucleotide(s), of stabilized ribozyme analog(s) and an RNA ligase, and/or of stabilized ribozyme analog(s) and facilitator oligonucleotide(s). The amount of stabilized ribozyme analog, or of ribozyme analog and facilitator oligonucleotide in the container may be sufficient for one therapeutic dose or assay. Alternatively, the amounts of the kit constituents may be concentrated such that only small aliquots need be sampled at one time from the container when used, for example, to cleave RNA molecules in vitro. The kits must preserve the ribozyme analog(s), facilitator oligonucleotides, and RNA ligase in active form. Any RNA ligase capable of covalently joining single stranded RNA molecules containing 5'-phosphate and 3'-hydroxyl termini is useful. One such ligase is bacteriophage T4 RNA ligase.

The present invention also provides therapeutic formulations containing a stabilized ribozyme analog, or a stabilized ribozyme analog and a facilitator oligonucleotide(s) useful for treatment. These therapeutic formulations must be administered to individuals in a manner capable of delivering the ribozyme analog and/or ribozyme analog and facilitator oligonucleotide initially into the body and subsequently into any number of target cells.

One mode of administration is via a therapeutic formulation which contains at least one stabilized ribozyme analog, as described above, along with a physiologically acceptable carrier. Some therapeutic formulations contain more than one type of ribozyme analog of the invention, and some include facilitator oligonucleotides.

As used herein, a "physiologically acceptable carrier" includes any and all solvents, dispersion media, coatings, antibacterial and antifungal agents, isotonic and absorption-delaying agents, and agents which improve oligonucleotide uptake, and the like. The use of such media and agents for pharmaceutically active substances is well known in the art. Except, insofar as any conventional media or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The therapeutic formulations of the invention may be administered parenterally, orally, by inhalation of spray, or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques.

The amount of active ribozyme analog that may be combined with the carrier materials to produce a single dosage form will vary depending upon the host treated and the particular mode of administration. It will be understood that the specific dose level for any particular patient will depend upon a variety of factors including the activity of the specific composition employed, the age, body weight, general health, sex, diet, time of administration, route of administration, and severity of the particular disease undergoing therapy.

The stabilized ribozyme analogs of the invention, themselves, or in a therapeutic formulation may be administered or utilized for any purpose known to those with skill in the art that a ribozyme or antisense oligonucleotide may be used. For example, cells infected with a virus may be treated with a ribozyme analog having flanking sequences complementary to nucleotide sequences of a particular mRNA corresponding to a viral gene in order to hinder the expression of that gene. Similarly, ribozyme analogs may be administered to stop the expression of cancer-related genes, or of any gene which is being overexpressed in vitro or in vivo. Ribozyme analogs are also useful in probing the function of a particular gene in vitro or in vivo, for example, by knocking out its function and observing the result.

Stabilized ribozyme analogs according to the invention are useful as RNA-specific restriction endonucleases, and as such, in combination with RNA ligases, allow for the preparation of recombinant RNA molecules.

The following examples illustrate the preferred modes of making and practicing the present invention, but are not meant to limit the scope of the invention since alternative methods may be utilized to obtain similar results.

EXAMPLES

1. Synthesis of Oligonucleotides

Substrate RNA, radiolabelled internally using $[\alpha^{-32}P]$ ATP, was prepared as described by Goodchild and Kohli (*Arch. Biochem. Biophys.* (1991) 284:386–391) using T7 RNA polymerase and chemically synthesized single-stranded templates with a double-stranded promoter (Milligan et al. (1987) *Nucleic Acids Res.* 15: 8783–8798). Oligodeoxynucleotides were synthesized using standard automated phosphoramidite procedures (Atkinson et al. in *Oligonucleotide Synthesis. A Practical Approach* (Gait, ed.) IRL Press, Washington, D.C. (1985) pages 35–81), then purified by polyacrylamide gel electrophoresis.

Concentrations of radiolabelled substrate were determined from the specific activity of the $[\alpha^{-32}P]ATP$ used for labelling. Concentrations of unlabelled RNA were determined spectroscopically from the absorption at 260 nm. Extinction coefficients at this wavelength were determined from the sum of the coefficients of the component nucleotides allowing for the hypochromicity of the RNA observed when a sample was digested to completion using snake venom phosphodiesterase and bacterial alkaline phosphatase.

2. Chemical Synthesis of Ribozyme Analog

Ribozymes were synthesized on a 1 μmol scale using the automated solid-support phosphoramidite method with commercial 2'-O-silyl nucleoside phosphoramidites (Usman et al. (1987) *J. Amer. Chem. Soc.* 109:7845–7854). Products were cleaved from the support and deblocked using concentrated ammonium hydroxide: ethanol (3:1 v/v) at 55° C. for 16 hours. The supernatant solution was divided into halves which were processed separately. After evaporation of solvent, each half of the product was dissolved in a solution of tetrabutylammonium fluoride (TBAF) in 1M tetrahydrofuran (THF) (0.4 ml) and kept in the dark at room temperature for 16–24 hours to remove silyl groups. The solution was cooled in ice and treated with ice cold 50 nM Tris-HCl, pH 7.4 (0.4 ml). Following addition of loading dye (0.8 ml of 95% formamide in water containing 0.05% by weight of Orange G), the solution was heated to 95° C., cooled, and applied directly to a polyacrylamide gel for purification by electrophoresis as described for substrate RNA (Goodchild et al. (1991) *Arch. Biochem. Biophys.* 284:386–391).

4. Preparation of Facilitator Oligonucleotide

Facilitator oligonucleotides which contain unmodified (phosphodiester-linked) deoxyribonucleotides were synthesized on an automated DNA synthesizer (Applied BioSystems, Foster City, Calif.) on a 1.0 μmole scale using standard H-phosphonate chemistry as described in U.S. Pat. No. 5,149,789, or using standard phosphoramidite chemistry as described by Beaucage (*Meth. Mol. Biol.* (1993) 20:33–61) or Uhlmann et al. (*Chem. Rev.* (1990) 90:534–583).

5. Cleavage Activity Assay

A solution (45 μl) containing substituted ribozyme analog or ribozyme control R22 (final concentration 0.025 μM), substrate RNA (e.g., S12; final concentration, 0.5 μM) and facilitator where appropriate (final concentration 1.0 μM) in 50 nM Tris-HCl (pH 7.4) was brought to the reaction temperature for 10 minutes. Reactions were initiated by the addition of 200 mM $MgCl_2$ (5 μl; final concentration 20 mM). After the indicated times, aliquots of 5 μl of the reaction were added to 10 μl of loading dye (95% formamide in water containing 0.05% by weight of Orange G) and put on ice. Samples were denatured by heating at 95° C. for 2 minutes and analyzed by electrophoresis on 15% polyacrylamide gel containing 8M urea. Radioactive bands were quantitated using a phosphorimager (Molecular Dynamics, Sunnyvale, Calif.). Representative results are shown in FIG. 6A to 6D.

6. Stability Assay

Figure 4:
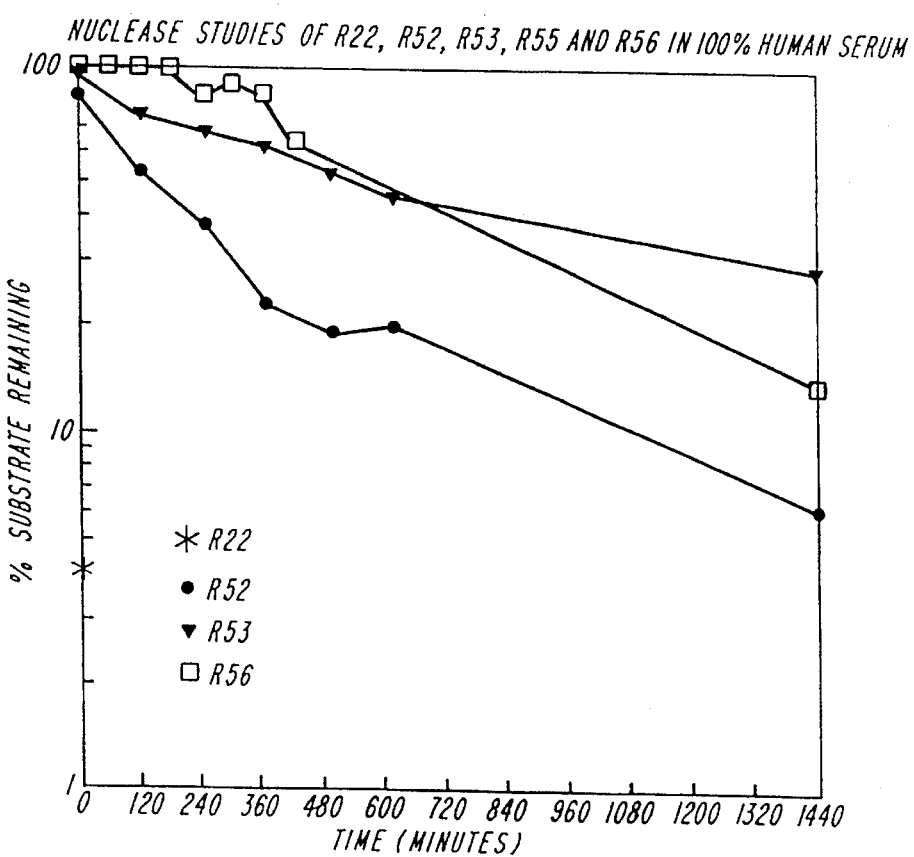
FIG. 4 is a graphic representation of the stability of representative stabilized ribozyme analogs of the invention in human serum.

The following procedure was used to examine the half-life of ribozymes in human serum. A solution (50 μl) containing 5'-[$^{32}$P] end-labelled ribozyme (40,000–150,000 cpms) and tRNA (final concentration of 300 μM) in H$_2$O was prepared. 5 μl of the solution was removed and added to 20 μl of loading dye (9M urea, 100 mM EDTA in H$_2$O) containing 0.05% by weight Orange G) and placed on dry ice. The remaining 45 μl was evaporated to dryness. The resulting pellet was dissolved in 45 μl human serum (Sigma Chemical Co., St. Louis, Mo.) and incubated at 37° C. At indicated times, aliquots of 5 μl of the reaction were added to 20 μl of loading dye and placed on dry ice. Samples were denatured by heating at 95° C. for 2 minutes and analyzed by electrophoresis on 15% polyacrylamide gel containing 8M urea. Representative results are shown in FIG. 4.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear RNA ( i i ) MOLECULE TYPE: RNA ( i i i ) HYPOTHETICAL: NO ( i v ) ANTI-SENSE: YES ( x i ) SEQUENCE DESCRIPTION: SEQ ID NO:1:

AAUACUCUGA UGAGGCCGUU AGGCCGAAAC GCUC      34

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear RNA ( i i ) MOLECULE TYPE: RNA ( i i i ) HYPOTHETICAL: NO ( i v ) ANTI-SENSE: YES ( x i ) SEQUENCE DESCRIPTION: SEQ ID NO:2:

UACUCUGAUG AGGCCGUUAG GCCGAAACGC UC      32

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear RNA ( i i ) MOLECULE TYPE: RNA ( i i i ) HYPOTHETICAL: NO ( i v ) ANTI-SENSE: YES ( x i ) SEQUENCE DESCRIPTION: SEQ ID NO:3:

| | | | | |
|---|---|---|---|---|
| UCAAAUACU | CUGAUGAGGC | CGUUAGGCCG | AAACGCUCAA | GA 42 |

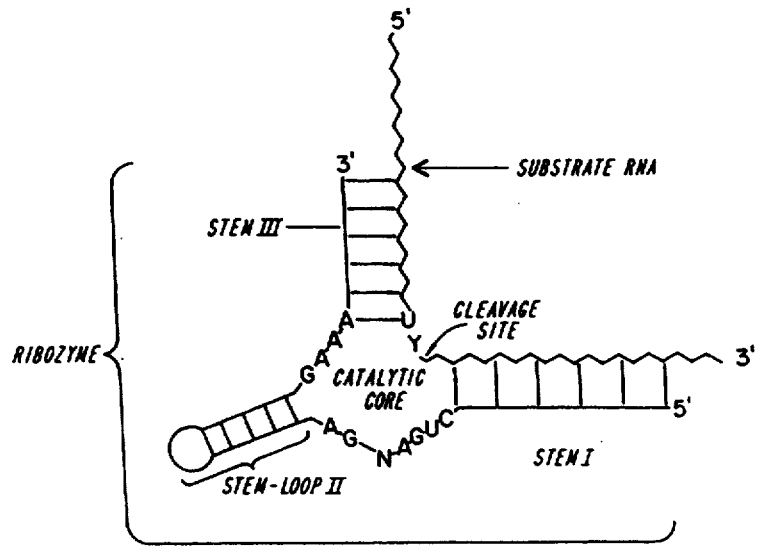

What is claimed is:

1. A stabilized ribozyme analog comprising:

(a) a helix II having a 3' terminus and a 5' terminus and comprising a stem region and a loop region, the stem region having a 3' terminus and a 5' terminus and comprising two to twelve 3' to 5' covalently-linked, self-hybridized nucleotides, and the loop region being covalently linked to the stem region at the 3' and 5' termini of the loop region, and comprising at least two 3' to 5' covalently-linked nucleotides including at least two modified nucleotides at Haseloff positions L2.2 and L2.3 which are purines, 2'-O-alkylated, or a combination thereof;

(b) first and second catalytic core regions, each having a 3' terminus and a 5' terminus, the first catalytic core region comprising seven 3' to 5' covalently-linked nucleotides and the second catalytic core region comprising three 3' to 5' covalently-linked nucleotides, the first catalytic core region further comprising three to seven modified nucleotides, the modified nucleotides being at least at Haselhoff positions 3 and 4 which are 2'-O-alkylated and at at Haselhoff position 7 which is a purine or is 2'-O-alkylated, the 3' terminus of the first catalytic core region being covalently linked to the 5' terminus of the stem region, and the 5' terminus of the second catalytic core region being covalently linked to the 3' terminus of the stem region; and (c) first and second flanking regions, each comprising four to fifty 3' to 5' covalently-linked purine and pyrimidine nucleotides, at least one of which is 2'-O-alkylated, and each having a 3' terminus and a 5' terminus, the first flanking region being complementary to a first target region of a substrate RNA molecule, and the second flanking region being complementary to a second target region of the substrate RNA molecule, the 3' terminus of the first flanking region being covalently linked to the 5' terminus of the first nucleotidic core region, and the 5' terminus of the second flanking region being covalently linked to the 3' terminus of the second nucleotidic core region.

2. The ribozyme analog of claim 1 wherein at least one of the self-hybridized nucleotides in the stem region is modified, the modified nucleotide being a purine or 2'-O-alkylated.

3. The ribozyme analog of claim 2 wherein the self-hybridized nucleotides at Haseloff positions 10.3, 10.4, 11.1, and 11.2 of the stem region are modified.

4. The ribozyme analog of claim 2 wherein a pyrimidine in the stem region is 2'-O-alkylated.

5. The ribozyme analog of claim 2 wherein all of the self-hybridized nucleotides in the stem region are modified.

6. The ribozyme analog of claim 1 wherein all of the nucleotides in the loop region are modified.

7. The ribozyme analog of claim 5 wherein all of the nucleotides in the loop region are modified.

8. The ribozyme analog of claim 1 wherein all of the nucleotides in the first flanking region are 2'-O-alkylated.

9. The ribozyme analog of claim 1 wherein all the nucleotides in the second flanking region with the exception of the nucleotide at position 15.1 are 2'-O-alkylated.

10. The ribozyme analog of claim 8 wherein all the nucleotides in the second flanking region are 2'-O-alkylated with the exception of the nucleotide at Haseloff position 15.1.

11. The ribozyme analog of claim 10 further comprising at least one modified nucleotide in the stem region.

12. The ribozyme analog of claim 11 wherein all of the nucleotides in the stem region are modified.

13. The ribozyme analog of claim 12 wherein all of the nucleotides in the loop region are modified.

14. The ribozyme analog of claim 1 wherein at least two nucleosides are linked by an alkylphosphonate internucleoside linkage.

15. The ribozyme analog of claim 1 wherein at least two nucleosides are linked by a phosphoramidate internucleoside linkage.

16. The ribozyme analog of claim 1 wherein the first and second flanking regions each comprise at least four nucleosides.

17. The ribozyme analog of claim 16 wherein the first and second flanking regions each comprise at least six nucleotides.

18. The ribozyme analog of claim 1 wherein at least four nucleotides in the first flanking region are complementary to a first set of at least four nucleotides of a target RNA, and at least four nucleotides in the second flanking region are complementary to a second set of at least four nucleotides of a target RNA, the first set and the second set being exclusive of each other.

19. The ribozyme analog of claim 1 wherein the 2'-O-alkylated nucleotides are selected from the group consisting of 2'-O-methylated, 2'-O-ethylated, 2'-O-propylated, and 2'-O-butylated nucleotides.

20. The ribozyme analog of claim 19 wherein the 2'-O-alkylated nucleotides are 2'-O-methylated nucleotides.

21. The ribozyme analog of claim 1 wherein the nucleosides in the loop region and the first and second flanking regions are covalently linked with internucleoside linkages selected from the group consisting of phosphodiester, alkylphosphonate, phosphorothioate, phosphorodithioate, alkylphosphonothioate, phosphoramidate, phosphate ester, carbamate, carbonate, acetamidate, carboxymethyl ester, and a combination thereof.

22. A kit comprising the stabilized ribozyme analog of claim 1.

23. The kit of claim 22 further comprising a facilitator oligonucleotide.

24. The kit of claim 22 further comprising an RNA ligase.

25. A kit comprising the ribozyme analog of claim 9.

26. The kit of claim 25 further comprising a facilitator oligonucleotide.

27. The kit of claim 25 further comprising an RNA ligase.

28. The ribozyme analog of claim 4 wherein the pyrimidines in the stem region are 2'-O-alkylated.

* * * * *

UNITED STATES PATENT AND TRADEMARK OFFICE
CERTIFICATE OF CORRECTION

PATENT NO.    : 5,545,729

DATED         : August 13, 1996

INVENTOR(S)   : John Goodchild, et. al.

Page 1 of 5

It is certified that error appears in the above-identified patent and that said Letters Patent is hereby corrected as shown below:

The Title Page, showing an illustrative figure, should be deleted and substitute therefor the attached Title Page.

Drawings:

Delete Figures 2, 3A, 3B, 3C, and 3D and substitute therefor Figs. 2, 3A, 3B, 3C, and 3D as shown on the attached pages.

Signed and Sealed this

Third Day of February, 1998

*Attest:*

BRUCE LEHMAN

*Attesting Officer*    *Commissioner of Patents and Trademarks*

United States Patent [19]
Goodchild et al.

[11] Patent Number: 5,545,729
[45] Date of Patent: Aug. 13, 1996

[54] STABILIZED RIBOZYME ANALOGS

[75] Inventors: John Goodchild, Westborough; Steven M. Nesbitt, Worcester, both of Mass.

[73] Assignee: Hybridon, Inc., Worcester, Mass.

[21] Appl. No.: 361,687

[22] Filed: Dec. 22, 1994

[51] Int. Cl.[6] .......................... C07H 21/04; C12Q 1/68; C12Q 1/70; A61K 48/00
[52] U.S. Cl. .................... 536/24.5; 435/6; 435/5
[58] Field of Search .................. 435/6, 5; 514/44; 536/24.5

[56] References Cited

FOREIGN PATENT DOCUMENTS

| | | |
|---|---|---|
| W092/07065 | 4/1992 | WIPO. |
| W093/15194 | 8/1993 | WIPO. |
| W093/15187 | 8/1993 | WIPO. |
| W094/10301 | 5/1994 | WIPO. |
| W094/12633 | 6/1994 | WIPO. |

OTHER PUBLICATIONS

Haseloff et al. (1988) *Nature* 334:585–591.
Buzayan et al. (1990) *Nucleic Acids Res.* 18:4447–4451.
Dahm et al. (1990) *Biochim.* 72:819–23.
Goodchild (1990) *Bioconjugate Chem.* 1:165–187.
Odai et al. (1990) *FEBS Lett.* 267:150–152.
Perreault et al. (1990) *Nature* 344:565–567.
Ruffner et al. (1990) *Nucleic Acids Res.* 18:6025–6029.
Goodchild et al. (1991) *Arch. Biochem. Biophys.* 284:386–391.
Koisumi et al. (1991) *Biochem.* 30:5145–5150.
Olsen et al. (1991) *Biochem.* 30:9735–9741.
Perreault et al. (1991) *Biochem.* 30:4020–4025.
Pieken et al. (1991) *Science* 253:314–317.
Agrawal et al. (1992) *Trends Biotechnol.* 10:152–158.
McCall et al. (1992) *Proc. Natl. Acad. Sci. (USA)* 89:5710–5714.
Paolella et al. (1992) *Embo J.* 11:1913–1919.
Benseler et al. (1993) *J. Am. Chem. Soc.* 115:8483–8484.
Ma et al. (1993) *Biochem.* 32:1751–1758.
Ma et al. (1993) *Nucleic Acids Res.* 21:2585–2589.
Thomson et al. (1993) *Nucleic Acids Res.* 21:5600–5603.
Tuschl et al. (1993) *Proc. Natl. Acad. Sci. (USA)* 90:6991–6994.
Ibirbarren et al, "2α-O-Alkyl Oligoribonucleotides as Antisense Probes", PNAS 87:7747–7751. Oct. 1990.
Sproat et al, "Highly Efficient Chemical Synthesis of 2α-O-Methyl-Oligoribonucleotides and Tetrabiotonylated Derivatives; Novel Probes Let are Resistant to Degradation by RNA or DNA Specific Nucleoses".

*Primary Examiner*—Stephanie W. Zitomer
*Assistant Examiner*—Dianne Rees
*Attorney, Agent, or Firm*—Lappin & Kusmer LLP

[57] ABSTRACT

Disclosed are stabilized ribozyme analogs having the ability to endonucleolytically cleave a sequence of 3' to 5' linked ribonucleotides. These ribozyme analogs include modifications at specific loop, catalytic core, and flanking region nucleotides which makes them more resistant to nucleases. Also disclosed are methods of preparing and utilizing the ribozyme analogs of the invention, and pharmaceutical formulations and kits containing such ribozyme analogs.

28 Claims, 8 Drawing Sheets